US011028062B2

(12) United States Patent
Qian et al.

(10) Patent No.: US 11,028,062 B2
(45) Date of Patent: Jun. 8, 2021

(54) CATALYTIC HYDROLYSIS AND DEHYDRATION OF SACCHARIDES

(71) Applicant: THE BOARD OF TRUSTEES OF THE UNIVERSITY OF ARKANSAS, Little Rock, AR (US)

(72) Inventors: Xianghong Qian, Fayetteville, AR (US); Ranil Wickramasinghe, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 15/568,672

(22) PCT Filed: Apr. 22, 2016

(86) PCT No.: PCT/US2016/028950
§ 371 (c)(1),
(2) Date: Oct. 23, 2017

(87) PCT Pub. No.: WO2016/172556
PCT Pub. Date: Oct. 27, 2016

(65) Prior Publication Data
US 2018/0155305 A1  Jun. 7, 2018

Related U.S. Application Data

(60) Provisional application No. 62/151,873, filed on Apr. 23, 2015.

(51) Int. Cl.
C07D 307/50    (2006.01)
C13K 1/02      (2006.01)
C13K 13/00     (2006.01)
C07D 307/48    (2006.01)
C07B 35/06     (2006.01)
C07C 53/128    (2006.01)

(52) U.S. Cl.
CPC ............ C07D 307/50 (2013.01); C07B 35/06 (2013.01); C07C 53/128 (2013.01); C07D 307/48 (2013.01); C13K 1/02 (2013.01); C13K 13/002 (2013.01)

(58) Field of Classification Search
CPC .................................................. C07D 307/50
USPC ....................................................... 549/488
See application file for complete search history.

(56) References Cited

U.S. PATENT DOCUMENTS 6,054,611 A *  4/2000  Farone ................. C07C 51/00
                                                    549/429
7,939,681 B2 *  5/2011  Zhao ................... C07D 307/46
                                                    549/488
8,324,376 B2 * 12/2012  Binder ................ C07D 307/28
                                                    549/488
8,772,515 B2 *  7/2014  Dumesic ............. C07D 307/50
                                                    549/429
9,079,171 B2 *  7/2015  Geremia .............. C08F 212/14
9,339,803 B2 *  5/2016  Wickramasinghe ........................
                                                    B01J 31/0225
2010/0004437 A1   1/2010  Binder et al.
2010/0317879 A1  12/2010  Zhao et al.
2012/0302767 A1  11/2012  Dumesic et al.
2014/0371340 A1  12/2014  Wickramasinghe et al.

OTHER PUBLICATIONS

Li, Energy Technol. 2013, 1, 151-756.*
Yu, Bioresource Technology 238 (2017) 716-732.*
Lin, RSC Adv., 2013, 3, 14379-14384.*
Wang, Green Chemistry, 14(9), 2012, 2506-2512.*
Menegazzo, Molecules 2018, 23, 2201, 1-18.*
Girisuta, Chemical Engineering Research and Design, 2006, 84(A5): 339-349.*
Girisuta, Ind. Eng. Chem. Res. 2007, 46, 1696-1708.*
Qian RSC Adv., 2013, 3, 24280-24287.*
Weingarten, Energy Environ. Sci., 2012, 5, 7559.*
International Search Report and Written Opinion of the International Application PCT/US2016/028950, dated Jul. 26, 2016, 8 pages.
Li et al., Polymeric Ionic Hybrid as Solid Acid Catalyst for the Selective Conversion of Fructose and Glucose to 5-Hydroxymethylfurfural, Energy Technology, vol. 1, 2013 [retrieved on Jun. 8, 2016). Retrieved from the Internet: <URL: https://www.researchgate.net/profile/Song_Yang4/publication/264223422_Polymeric_Ionic_Hybrid_as_Solid_Acid_Catalyst_for_the_Selective_Conversion_of_Fructose_and_Glucose_to_5-Hydroxymethylfurfural/links/55c87fa808aeca74 7d66c581.pdf>. pp. 151-156.
Tian et al., Simulation of the Properties of 1-Ethyl-3-Methyl-Imidazolium Chloride/Chloroaluminate Ionic Liquids: Concentration and Temperature Dependence, Advanced Materials Research, vols. 457-458, Jan. 2012 [retrieved on Jun. 9, 2016). Retrieved from the Internet: <URL: http://www.scientific.net/AMR.457-458.249>. see abstract.
N,N-Dimethylacetamide, Chemical Book, Mar. 23, 2014 [retrieved on Jun. 9, 2016). Retrieved from the Internet: <URL:http://web.archive.org/web/20140323171856/http://www.chemicalbook.com/ChemicalProductProperty_EN_CB8853004.htm>. entire document.

* cited by examiner

Primary Examiner — Nizal S Chandrakumar
(74) Attorney, Agent, or Firm — J. Clinton Wimbish; Nexsen Pruet, PLLC

(57) ABSTRACT

In one aspect, methods of HMF production are described herein. A method of HMF production, in some embodiments, comprises providing a saccharide feedstock including glucose and bringing the saccharide feedstock into contact with a solid state catalytic structure at a temperature sufficient to effectuate dehydration of the glucose to provide HMF. The solid state catalytic structure comprises a substrate having one or more surfaces functionalized with saccharide solubilization functionalities and acid functionalities, wherein the saccharide solubilization functionalities comprise one or more imidazolium salts pendant along chains of a first polymeric species attached to the substrate surface.

20 Claims, 12 Drawing Sheets

US 11,028,062 B2

CATALYTIC HYDROLYSIS AND DEHYDRATION OF SACCHARIDES

RELATED APPLICATION DATA

The present application is a national stage application under 35 U.S.C. § 371 of International Application No. PCT/US2016/028950, filed Apr. 22, 2016, which claims priority pursuant to 35 U.S.C. § 119(e) to U.S. Provisional Patent Application Ser. No. 62/151,873 filed Apr. 23, 2015, each of which are incorporated herein by reference in their entireties.

FIELD

The present invention relates to the catalytic hydrolysis and dehydration of saccharides and, in particular, to the catalytic hydrolysis of cellulose and hemicellulose followed by catalytic dehydration of glucose and xylose to hydroxymethylfurfural (HMF) and furfural respectively.

BACKGROUND

Biofuel derived from lignocellulosic biomass is one of the leading renewable energy candidates to replace fossil-based transportation fuels. The Biofuels Initiative implemented by the United States government aims to make cellulosic biofuel cost competitive with gasoline and to replace up to 30 percent of current gasoline consumption by 2030. Cellulosic biomass represents an abundant renewable resource for the production of bio-based products and biofuels.

HMF is a critical and versatile intermediate for converting biomass to liquid alkanes and many other value-added products. The key bottleneck for lignocellulosic-derived biofuels is the lack of technology for efficient and cost-effective conversion of abundant biomass into liquid fuels. The conversion yields from biomass carbohydrates, particularly glucose, remain critical issues. The economic viability for converting biomass via HMF to liquid alkanes and other value added chemicals depends strongly on developing enabling technologies that produce high yields of HMF from glucose. Currently the HMF yield from glucose is limited and extremely sensitive to processing conditions using the conventional acid dehydration process.

SUMMARY

In one aspect, methods of HMF production are described herein which, in some embodiments, can overcome low yields systemic to prior techniques. For example, a method of HMF production comprises providing a saccharide feedstock including glucose and bringing the saccharide feedstock into contact with a solid state catalytic structure at a temperature sufficient to effectuate dehydration of the glucose to provide HMF. Moreover, in some embodiments, the solid state catalytic structure can further participate in the production of levulinic acid from HMF. In such embodiments, HMF is brought into contact with the solid state catalytic structure at a temperature sufficient to effectuate production of levulinic acid from the HMF.

The solid state catalytic structure comprises a substrate having one or more surfaces functionalized with saccharide solubilization functionalities and acid functionalities, wherein the saccharide solubilization functionalities comprise one or more imidazolium salts pendant along chains of a first polymeric species attached to the substrate surface. In some embodiments, the saccharide feedstock also includes xylose for dehydration to furfural by the solid state catalytic structure. The solid state catalytic structure employs acid functionalities operable to participate in dehydration mechanisms of glucose and/or xylose. For example, the acid functionalities can include aryl sulfonic acid groups. In some embodiments, an aryl-sulfonic acid group comprises one or more ring substituents selected from the group consisting of —F, —Cl, —Br, $NO_2$, $NR^1R^2$, $OR^3$, wherein $R^1$-$R^3$ are independently selected from the group consisting of hydrogen, alkyl and alkenyl. Further, the acid functionalities can be pendant along chains of a second polymeric species attached to the substrate surface.

In another embodiment, a method of HMF production comprises providing a solution comprising saccharide feedstock including cellulose in an ionic liquid composition at a first temperature. The saccharide feedstock solution is brought into contact with a solid state catalytic structure comprising a substrate having one or more surfaces functionalized with saccharide solubilization functionalities and acid functionalities, wherein the saccharide solubilization functionalities comprise one or more imidazolium salts pendant along chains of a first polymeric species attached to the substrate surface. Cellulose of the saccharide feedstock is hydrolyzed by the acid functionalities of the solid state catalytic structure to provide glucose feedstock in the ionic liquid composition. The temperature of the ionic liquid composition is altered to a second temperature, and the glucose feedstock is brought into contact with the solid state catalytic structure to effectuate dehydration of the glucose to provide HMF. Further, the temperature of the ionic liquid can be altered to a third temperature to effectuate production of levulinic acid from the HMF.

In some embodiments, the saccharide feedstock also includes hemicellulose. In such embodiments, the hemicellulose is brought into contact with the solid state catalytic structure and hydrolyzed to provide xylose feedstock in the ionic liquid composition. The xylose feedstock is brought into contact with the solid state catalytic structure at the second temperature to effectuate dehydration of the xylose to furfural. Therefore, methods employing solid state catalytic structures described herein provide a facile and efficient pathway for converting lignocellulosic materials to HMF and furfural. Further, these methods can also enable the production of levulinic acid from HMF.

These and other embodiments are further described in the following detailed description.

DETAILED DESCRIPTION

Figure 1:
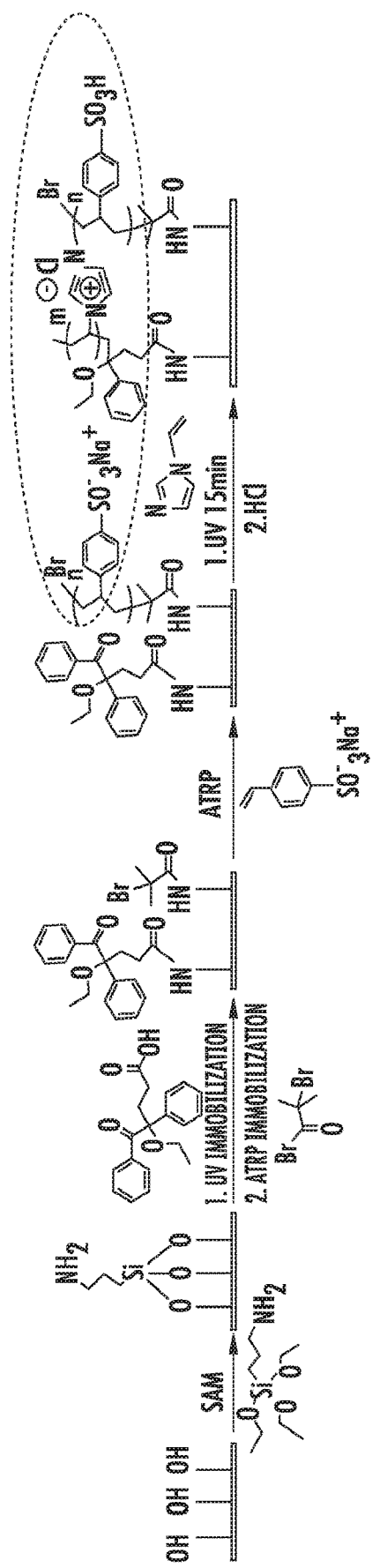
FIG. 1 illustrates substrate surface functionalization with a first polymer chain comprising pendant imidazolium salts and a second polymer chain comprising pendant aryl-sulfonic acid groups according to one embodiment described herein.

Embodiments described herein can be understood more readily by reference to the following detailed description, examples, and drawings. Elements, apparatus, and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In one aspect, methods of HMF production are described herein. A method of HMF production, in some embodiments, comprises providing a saccharide feedstock including glucose and bringing the saccharide feedstock into contact with a solid state catalytic structure at a temperature sufficient to effectuate dehydration of the glucose to provide HMF. The solid state catalytic structure comprises a substrate having one or more surfaces functionalized with saccharide solubilization functionalities and acid functionalities, wherein the saccharide solubilization functionalities comprise one or more imidazolium salts pendant along chains of a first polymeric species attached to the substrate surface.

Turning now to specific steps, a saccharide feedstock including glucose can be dissolved or dispersed in an ionic liquid composition. The ionic liquid composition, in some embodiments, consists solely of one or more ionic liquid species. Alternatively, the ionic liquid composition can comprise a mixture of ionic liquid with water or aprotic solvent. For example, the ionic liquid composition can comprise ionic liquid mixed with an aprotic solvent selected from valerolactone, acetonitrile and dimethylacetamide. Ionic liquid, such as [EMIM]Cl and/or [EMIM]Br, can be present in the mixture in any desired amount not inconsistent with the objectives of the present invention. In some embodiments, ionic liquid is present in the mixture in an amount of 20 vol. % to 80 vol. % with the balance water or aprotic solvent. As described in the examples below, [EMIM]Cl and/or [EMIM]Br can be present in the ionic liquid composition in an amount of 30 vol. % to 70 vol. % with the balance γ-valerolactone (GVL).

The ionic liquid composition provides a medium for bringing glucose of the saccharide feedstock into contact with the solid state catalytic structure at a temperature sufficient to effectuate dehydration of the glucose to provide HMF. In some embodiments, the ionic liquid composition is heated to a temperature in excess of 130° C. to facilitate glucose dehydration by the solid state catalytic structure. For example, the ionic liquid composition can be heated to a temperature of 135-150° C. to facilitate glucose dehydration by the solid catalytic structure. The ionic liquid composition can be further heated to effectuate production of levulinic acid from interaction of HMF with the solid catalytic structure. In some embodiments, the ionic liquid composition is heated to a temperature of at least 150° C. for levulinic acid production. Production of levulinic acid from HMF may also yield formic acid.

The solid state catalytic structure comprises a substrate having one or more surfaces functionalized with saccharide solubilization functionalities and acid functionalities, wherein the saccharide solubilization functionalities comprise one or more imidazolium salts pendant along chains of a first polymeric species attached to the substrate surface. In some embodiments, the one or more imidazolium salts is of the formula:

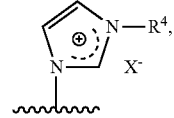

wherein ∿∿ is a point of attachment to the polymer chain, $X^-$ is a counterion and $R^4$ is selected from the group consisting of hydrogen, alkyl and alkenyl. Any counterion not inconsistent with the objectives of the present invention may be used. In some embodiments, the one or more imidazolium salts comprise imidazolium chlorides.

The substrate is also functionalized with acid functionalities operable to participate in the dehydration pathway of glucose and/or xylose. Suitable acid functionalities generally have a pKa ranging from about 1 to about 5. Acid functionalities can include aryl sulfonic acid groups. In some embodiments, an aryl-sulfonic acid group comprises one or more ring substituents selected from the group consisting of —F, —Cl, —Br, $NO_2$, $NR^1R^2$, $OR^3$, wherein $R^1$-$R^3$ are independently selected from the group consisting of hydrogen, alkyl and alkenyl. Further, the acid functionalities can be pendant along chains of a second polymeric species attached to the substrate surface. For example, polystyrene sulfonic acid (PSSA) can be employed for functionalizing the substrate surface with acid functionalities.

First polymer comprising saccharide solubilization functionalities and second polymer comprising acid functionalities can be randomly grafted onto the substrate surface. In some embodiments, catalytic activity of the solid state structure can be tuned by varying chain length and/or chain density of the first and second polymer. For example, longer chain second polymer containing acid functionalities, such as PSSA, can provide enhanced cellulose or hemicellulose hydrolysis and subsequent conversion to HMF and furfural. FIG. 1 illustrates substrate surface functionalization with a first polymer chain comprising pendant imidazolium salts and second polymer chain comprising pendant aryl-sulfonic acid groups according to one embodiment described herein.

The substrate of the catalytic structure can be formed of any material not inconsistent with the objectives of the present invention. In some embodiments, a substrate material is selected according to the ability to be functionalized with surface polymeric species described herein. In some embodiments, a substrate comprises an inorganic composition, such as an inorganic oxide or ceramic. For example, a substrate can be formed of one or more of alumina ($Al_2O_3$), silica ($SiO_2$), titania ($TiO_2$) and zirconia ($ZrO_2$). Alternatively, the substrate can be formed of an organic composition. In some embodiments, suitable polymers for the substrate are operable to be functionalized with first and second polymer described herein and demonstrate chemical, thermal and mechanical stabilities required for acid catalyzed reactions. In some embodiments, a catalytic membrane is formed from polyvinyl alcohol, polyvinyl chloride or polyacrylonitrile. A catalytic membrane can also be formed of oxygen plasma treated or oxygen plasma modified polymer. For example, a substrate can be formed of oxygen plasma treated polyolefin, such as polyethylene or polypropylene. A substrate, in some embodiments, is formed of oxygen plasma treated polystyrene. Oxygen plasma treatment of polymeric materials forming substrate of the catalytic structure can provide the polymeric materials moieties suitable for surface functionalization with a polymer having saccharide solubilization functionalities and acidic functionalities described herein.

In some embodiments, a substrate comprises an inorganic composition and an organic composition. In one embodiment, for example, a substrate is formed of a polymer coated metal or polymer coated ceramic.

Depending on application, the substrate can be porous or non-porous. In porous embodiments, the substrate can serve as a membrane for separating HMF and/or furfural from the saccharide feedstock and ionic liquid composition. For example, HMF and/or furfural can pass through the pore structure of the substrate for extraction into an organic phase. Accordingly, in porous embodiments, the substrate exhibits pore structure and size for passing HMF and furfural while excluding species of the saccharide feedstock. A porous substrate, for example, can be a nanofiltration membrane having a pore size distribution less than about 200 nm. In some embodiments, a nanofiltration membrane has a pore size distribution less than about 100 nm or less than about 20 nm. A nanofiltration membrane can also exhibit a pore size distribution ranging from about 0.5 nm to about 15 or from about 1 nm to about 10 nm. In some embodiments, pore surfaces of the substrate are functionalized with imidazolium salt first polymer and acid functionality second polymer.

Further, the substrate can have any desired shape. In some embodiments, the substrate is planar or sheet-like. Alternatively, the substrate can be tubular, convex, concave or combinations thereof, such as corrugated.

Additional solid state catalytic structures that can be used in methods described herein are provided in U.S. patent application Ser. No. 14/355,364 which is incorporated herein by reference in its entirety.

As described herein, the saccharide feedstock can also include xylose for dehydration to furfural by the solid state catalytic structure. As set forth in embodiments of the present application, saccharide feedstock can include polysaccharides such as cellulose and hemicellulose as well as monosaccharides including glucose, xylose and/or other reducing sugars.

Catalytic structures described herein exhibit a high degree of versatility permitting employment in a number of acid catalyzed schemes. Further, catalytic structures described herein can serve as a single architecture for conversion of cellulose and hemicellulose to HMF and furfural respectively. The catalytic structures may also participate in the production of levulinic acid and/or formic acid from HMF.

For example, in another embodiment, a method of HMF production comprises providing a solution comprising saccharide feedstock including cellulose in an ionic liquid composition at a first temperature. The saccharide feedstock solution is brought into contact with a solid state catalytic structure comprising a substrate having one or more surfaces functionalized with saccharide solubilization functionalities and acid functionalities, wherein the saccharide solubilization functionalities comprise one or more imidazolium salts pendant along chains of a first polymeric species attached to the substrate surface. Cellulose of the saccharide feedstock is hydrolyzed by the acid functionalities of the solid state catalytic structure to provide glucose feedstock in the ionic liquid composition. The temperature of the ionic liquid composition is altered to a second temperature, and the glucose feedstock is brought into contact with the solid state catalytic structure to effectuate dehydration of the glucose to provide HMF. In some embodiments, the ionic liquid is heated to provide the second temperature higher than the first temperature. For example, the ionic liquid can be heated to a temperature above 130° C. to effectuate glucose dehydration for HMF production. Further, the temperature of the ionic liquid can be altered to a third temperature to effectuate production of levulinic acid from the HMF. The third temperature can be higher than the second temperature and generally range from 150-160° C.

In some embodiments, the saccharide feedstock also includes hemicellulose. In such embodiments, the hemicellulose is brought into contact with the solid state catalytic structure and hydrolyzed to provide xylose feedstock in the ionic liquid composition. The xylose feedstock is brought into contact with the solid state catalytic structure at the higher second temperature to effectuate dehydration of the xylose to furfural. Therefore, solid state catalytic structures employed in methods described herein provide a facile and efficient pathway for converting lignocellulosic materials to HMF and furfural.

Additionally, in some embodiments of methods described herein, metal-based homogeneous catalyst such as $CrCl_2$/$CrCl_3$ or heterogeneous catalysts such as Sn beta or Sn/W can be used with solid state catalytic structures and/or ionic liquid compositions for the catalytic conversion of glucose to HMF.

Some embodiments described herein are further illustrated in the following non-limiting examples.

Example 1—Cellulose Hydrolysis

Ceramic substrates were functionalized according to the reaction scheme provided in FIG. 1 to provide solid state catalytic structures. Cellulose hydrolysis activity and glucose yield were determined for the catalytic structures as a function of identity of ionic liquid composition and reaction time. Table I provides the various ionic liquid compositions investigated for cellulose hydrolysis by the catalytic structures and corresponding the Figure illustrating the hydrolysis results.

TABLE I

Ionic Liquid Compositions

Figure 2:
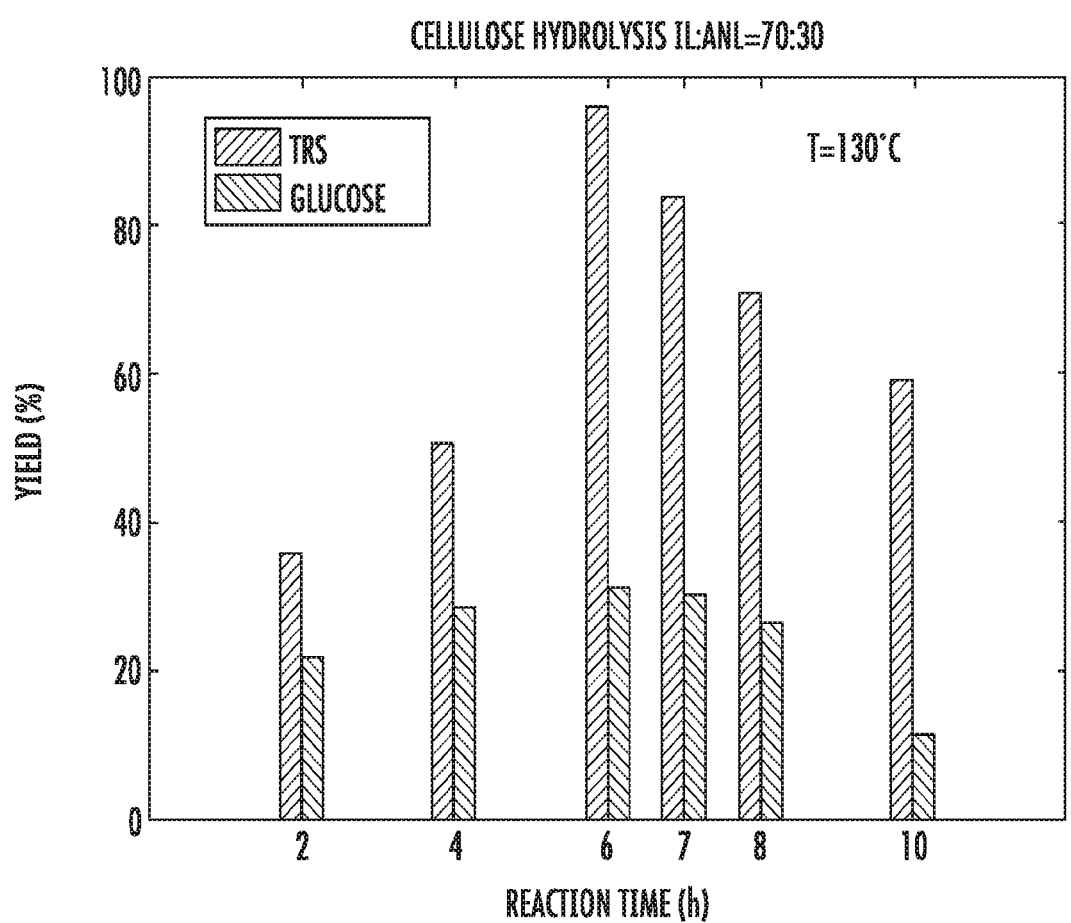
FIG. 2 illustrates cellulose hydrolysis and glucose yield of a solid state catalytic structure in contact with an ionic liquid composition comprising cellulose according to one embodiment described herein.
Figure 3:
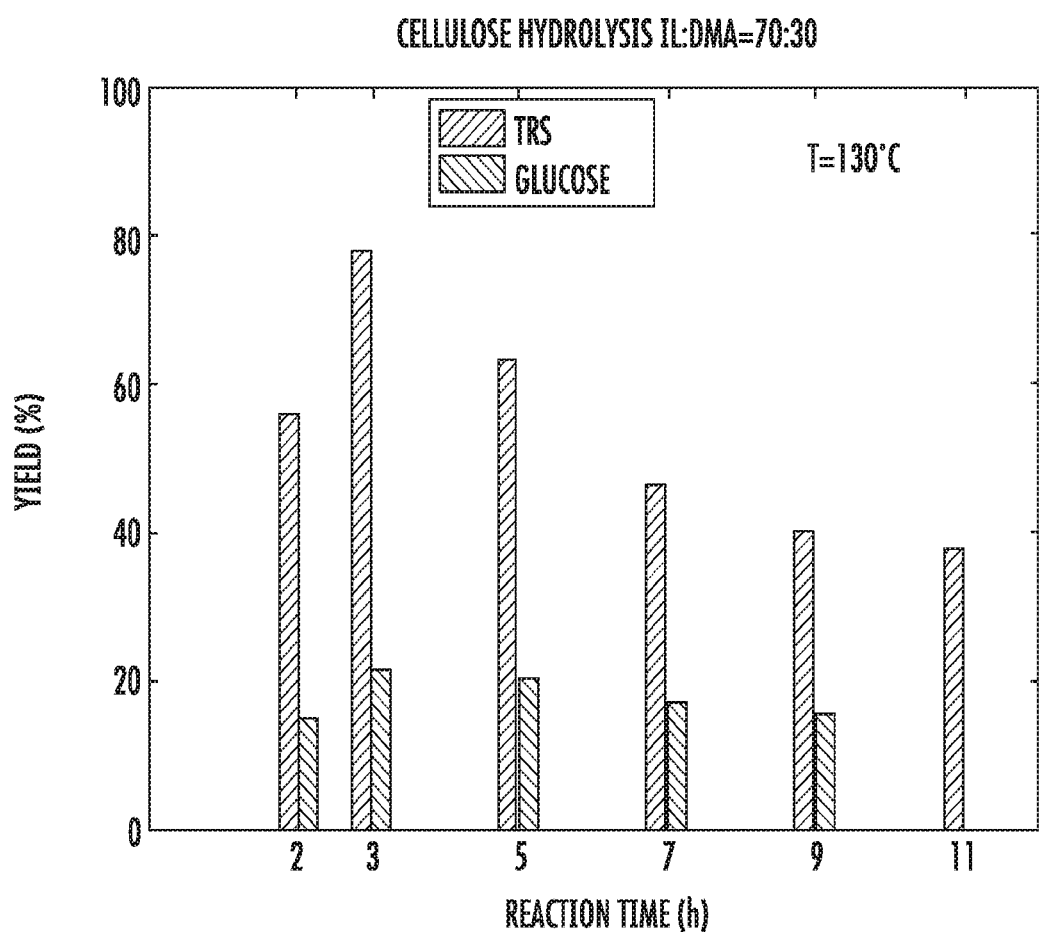
FIG. 3 illustrates cellulose hydrolysis and glucose yield of a solid state catalytic structure in contact with an ionic liquid composition comprising cellulose according to one embodiment described herein.
Figure 4:
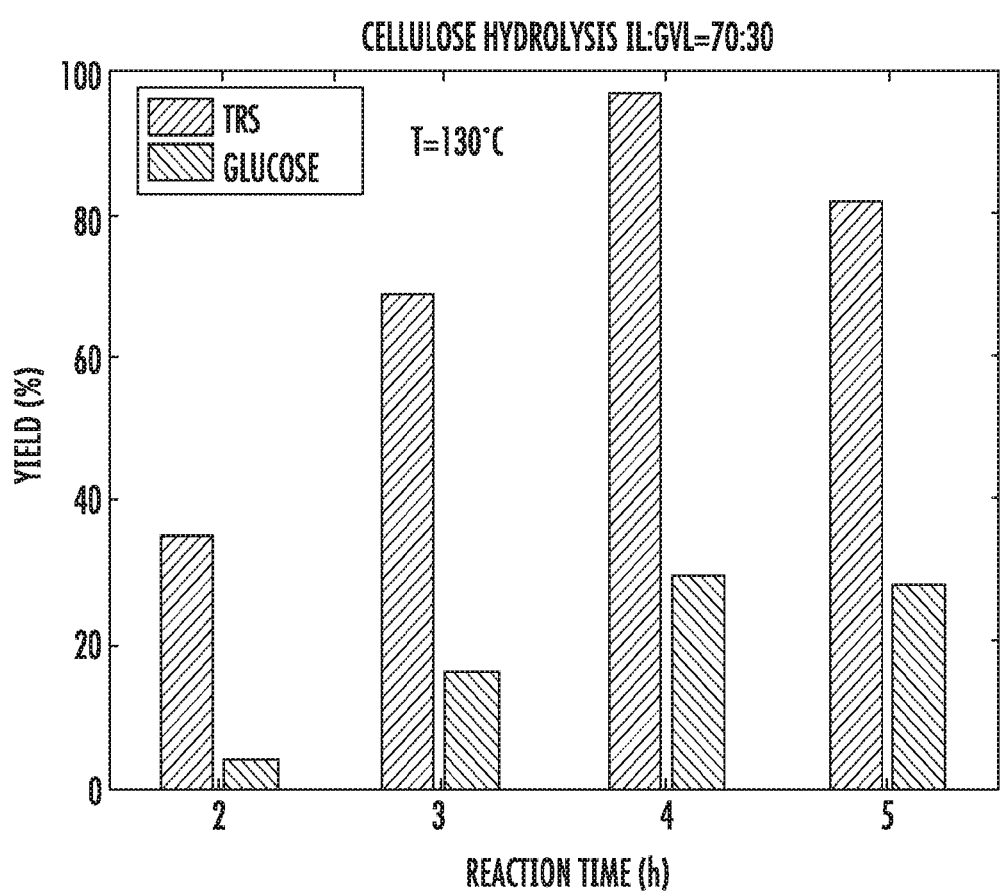
FIG. 4 illustrates cellulose hydrolysis and glucose yield of a solid state catalytic structure in contact with an ionic liquid composition comprising cellulose according to one embodiment described herein.
Figure 5:
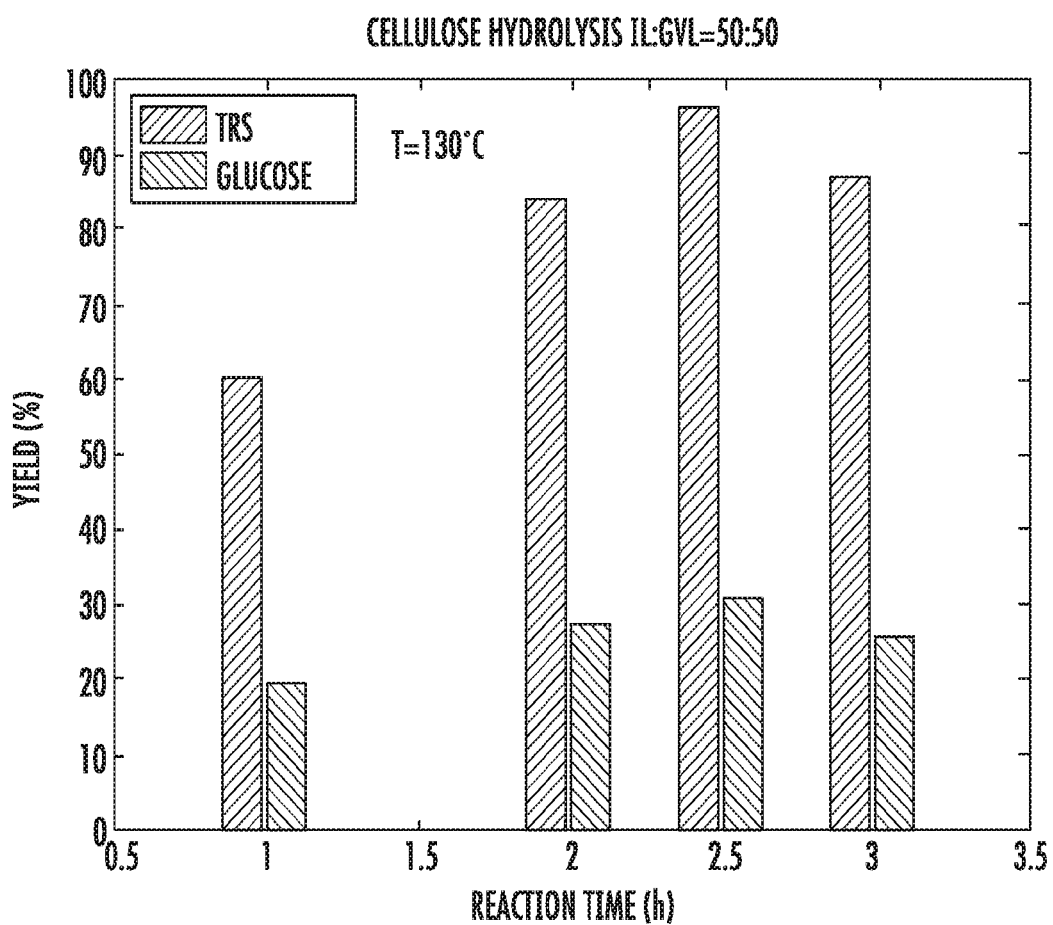
FIG. 5 illustrates cellulose hydrolysis and glucose yield of a solid state catalytic structure in contact with an ionic liquid composition comprising cellulose according to one embodiment described herein.

| Run | Ionic Liquid Composition | Result |
|-----|--------------------------|--------|
| 1 | 70% [EMIM]Cl; 30% Acetonitrile | FIG. 2 |
| 2 | 70% [EMIM]Cl; 30% Dimethylacetamide | FIG. 3 |
| 3 | 70% [EMIM]Cl; 30% γ-valerolactone | FIG. 4 |
| 4 | 50% [EMIM]Cl; 50% γ-valerolactone | FIG. 5 |

Example 2—Glucose Dehydration to HMF

Figure 6:
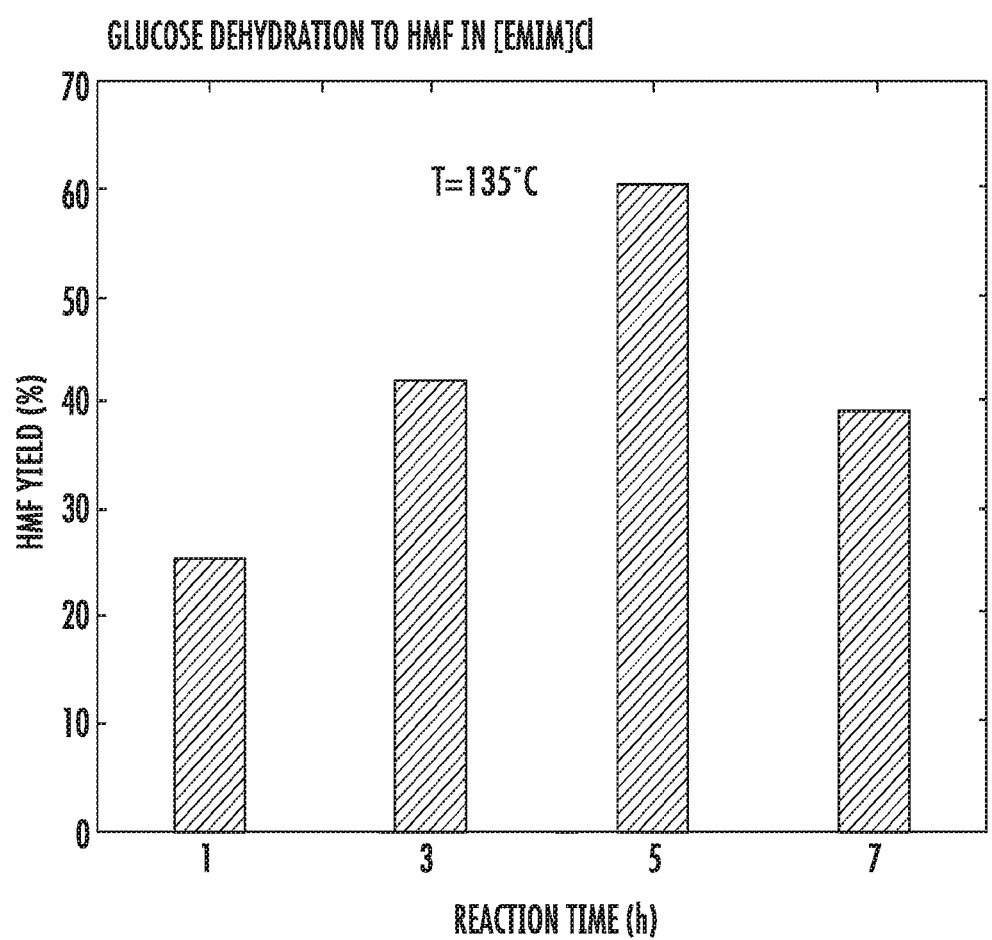
FIG. 6 illustrates glucose dehydration and HMF yield of a solid state catalytic structure in contact with an ionic liquid comprising glucose according to one embodiment described herein.

A ceramic substrate was functionalized according to the reaction scheme of FIG. 1 to provide a catalytic structure described herein. The catalytic structure was contacted with glucose in [EMIM]Cl at a temperature of 135° C. to determine HMF yield. The results are provided in FIG. 6.

Example 3—HMF Production from Cellulose

Figure 7:
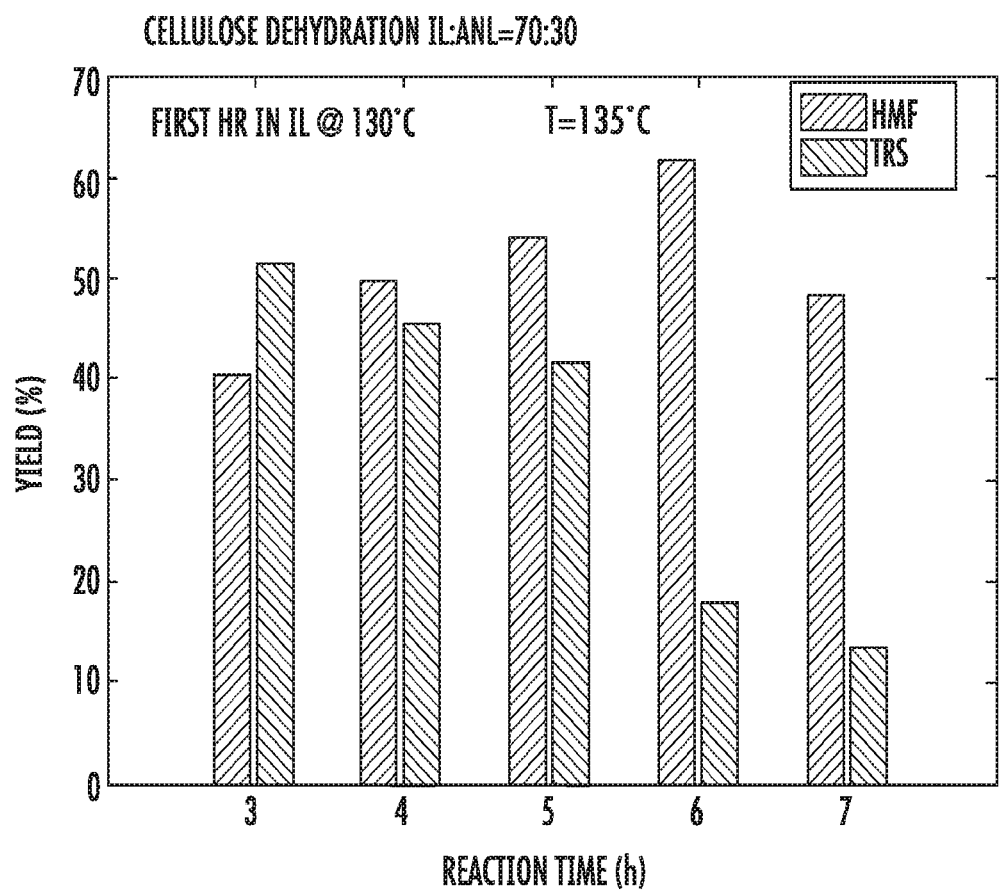
FIG. 7 illustrates HMF yield of a solid state catalytic structure in contact with an ionic liquid composition comprising cellulose according to one embodiment described herein.

A ceramic substrate was functionalized according to the reaction scheme of FIG. 1 to provide a catalytic structure described herein. The catalytic structure was contacted with cellulose in an ionic liquid composition of 70% [EMIM]Cl and 30% acetonitrile. Cellulose hydrolysis was conducted at 130° C. for one hour, followed by increasing the reaction temperature to 135° C. for the glucose dehydration reaction. Dehydration was conducted for 3 to 6 hours, and the results are provided in FIG. 7. Dehydration for 6 hours produced HMF yield in excess of 60%.

Example 4—HMF Production from Cellulose

Figure 8:
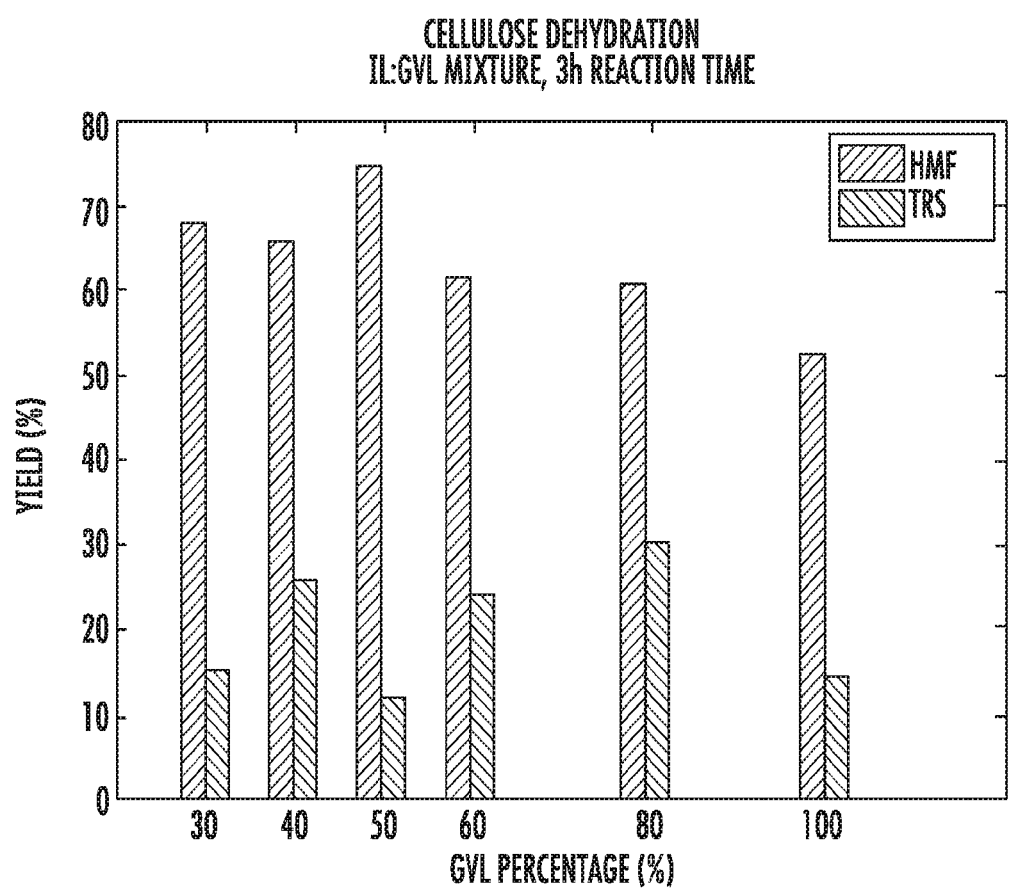
FIG. 8 illustrates HMF yields from solid state catalytic structures in contact with ionic liquid compositions with varying percentages of GVL according to some embodiments described herein.
Figure 9:
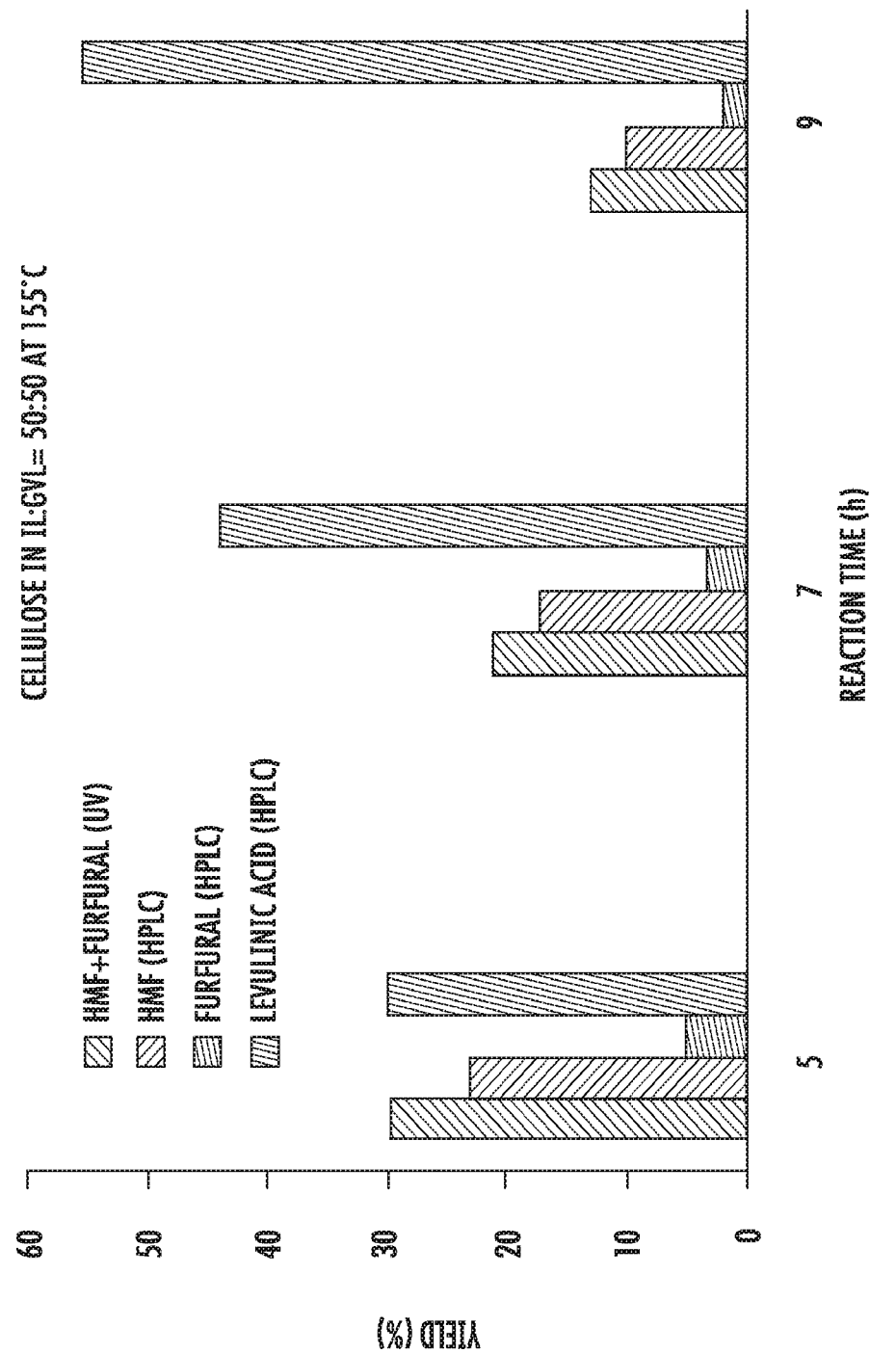
FIG. 9 illustrates levulinic acid yields from solid state catalytic structures in contact with ionic liquid compositions comprising HMF according to some embodiments described herein.
Figure 10:
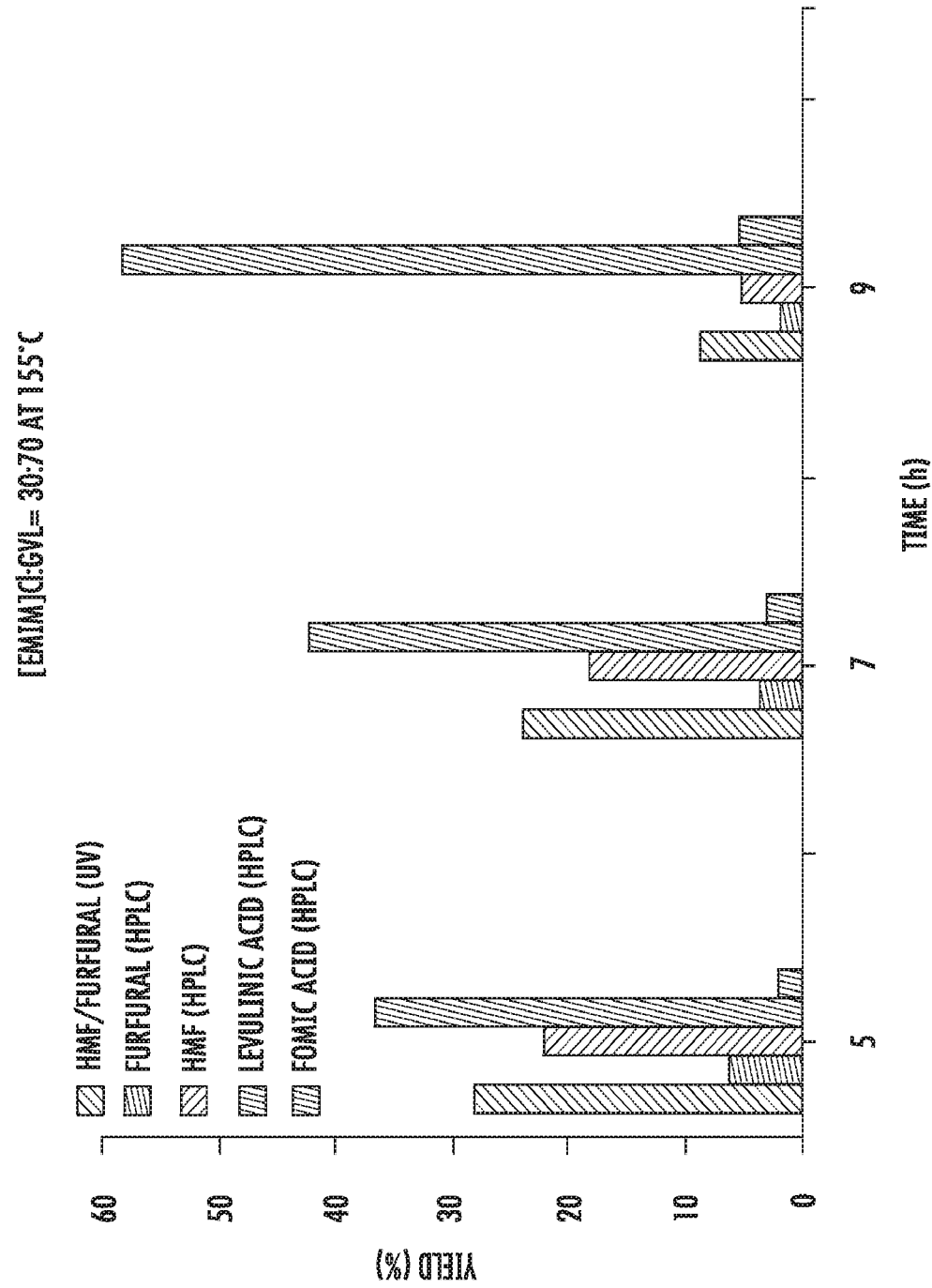
FIG. 10 illustrates levulinic acid yields from solid state catalytic structures in contact with ionic liquid compositions comprising HMF according to some embodiments described herein.
Figure 11:
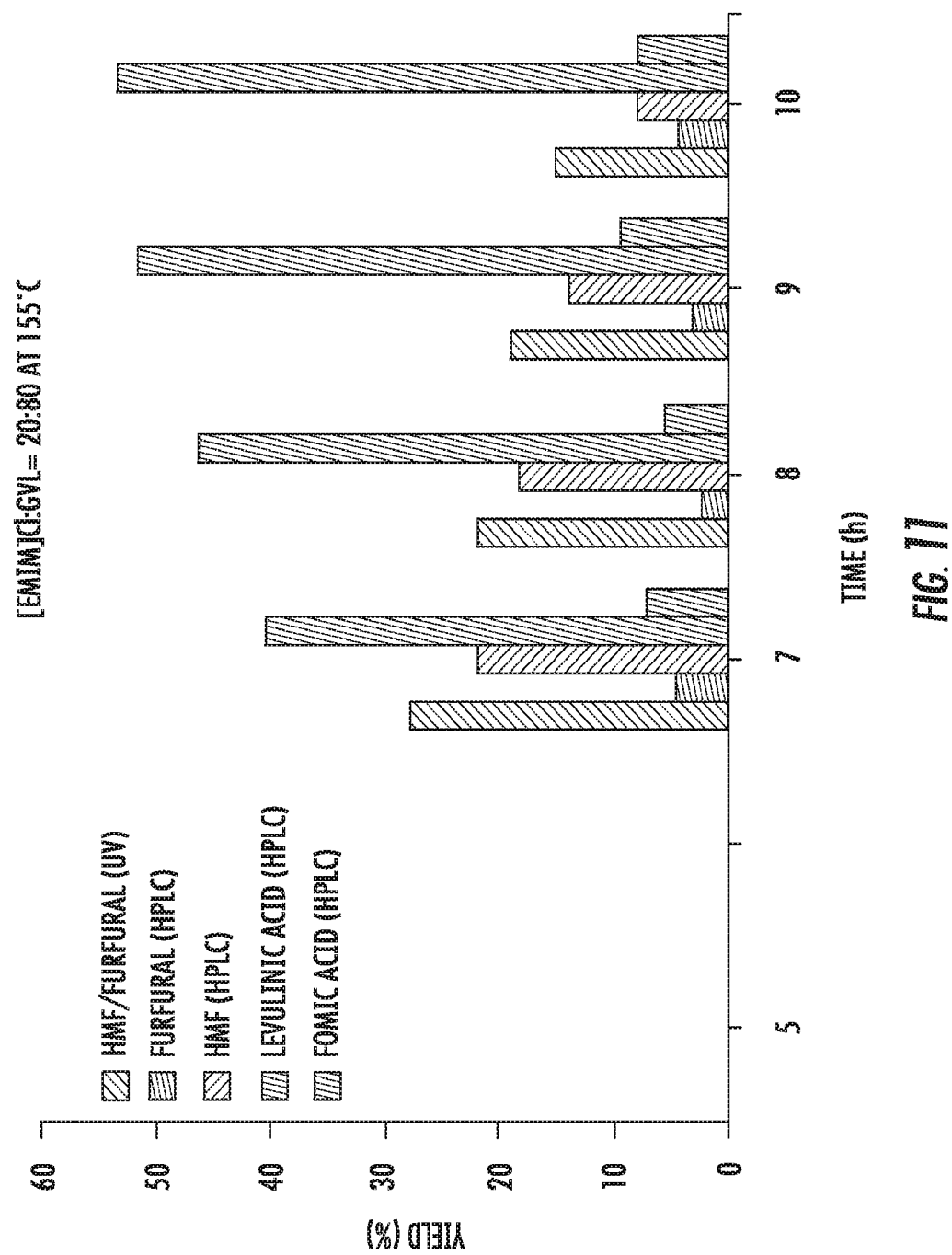
FIG. 11 illustrates levulinic acid yields from solid state catalytic structures in contact with ionic liquid compositions comprising HMF according to some embodiments described herein.
Figure 12:
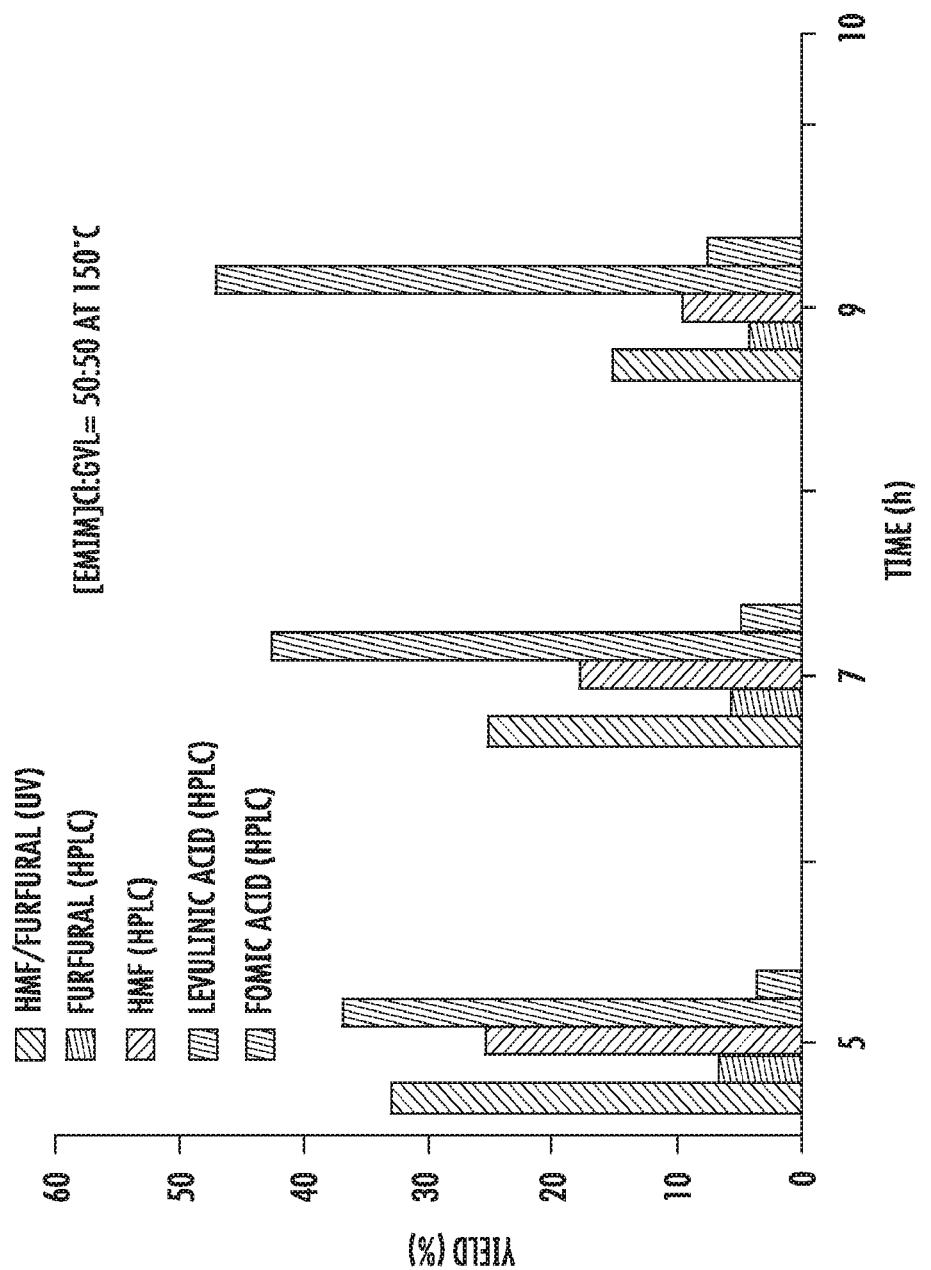
FIG. 12 illustrates levulinic acid yields from solid state catalytic structures in contact with ionic liquid compositions comprising HMF according to some embodiments described herein.

Ceramic substrates were functionalized according to the reaction scheme of FIG. 1 to provide catalytic structures described herein. The catalytic structures were contacted with cellulose in ionic liquid compositions with varying percentages of GVL according to Table II to determine HMF yield after 3 hours of reaction at 135° C. Results of the runs are provided in FIG. 8.

TABLE II

Ionic Liquid Compositions

| Run | Ionic Liquid Composition |
|-----|--------------------------|
| 1 | 70% [EMIM]Cl; 30% GVL |
| 2 | 60% [EMIM]Cl; 40% GVL |
| 3 | 50% [EMIM]Cl; 50% GVL |
| 4 | 40% [EMIM]Cl; 60% GVL |
| 5 | 20% [EMIM]Cl; 80% GVL |
| 6 | 100% GVL |

Example 5—Levulinic Acid Production 0.1 g of feedstock biomass (cellulose) in 10 mL mixture of 80:20, 70:30, or 50:50 [EMIM]Cl:GVL at were transferred into batch reactor. Silica membrane substrate (Atech disc) functionalized according to the reaction scheme of FIG. 1 was then also submerged into the solution. The batch reactor was tightly sealed and placed into sand bath. Reaction was conducted at 150° C. and 155° C. for 10-11 hours. After that, the reactor was cooled down to room temperature and diluted with fixed amount of water. The precipitated/un-dissolved solid was filtered, dried under vacuum oven. The total reducing sugar (TRS) was determined by DNS reagent. Concentration of mixture HMF/furfural was measured by UV spectrometer, wavelength 280 nm. Single component of HMF and furfural was then measured again with HPLC by using HiPlex Ca (Duo) column. The mobile phase is water and flow rate is at 0.6 ml/min. Temperature of the column is 80° C. and RID is at 45° C. Levulinic acid and formic acid concentration were measured by using HPLC, AMINEX HPX-87X column. The mobile phase is 0.008M sulfuric acid and flow rate is at 0.6 ml/min Temperature of the column is 55° C. and RID is at 55° C. Results of levulinic acid production are summarized in FIGS. 9-12.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of producing hydroxymethylfurfural (HMF) and levulinic acid comprising:
   providing a saccharide feedstock including glucose;
   bringing the saccharide feedstock into contact with a solid state catalytic structure at a first temperature sufficient to effectuate dehydration of the glucose to provide the HMF; and
   bringing the HMF into contact with the solid state catalytic structure at a second temperature sufficient to produce levulinic acid,
   wherein the solid state catalytic structure comprises a substrate having one or more surfaces functionalized with saccharide solubilization functionalities and acid functionalities,
   wherein the saccharide solubilization functionalities comprise one or more imidazolium halide salts pendant along chains of a first polymeric species attached to the substrate surface, and the acid functionalities are pendant along chains of a second polymeric species attached to the substrate surface, and
   wherein the second temperature is higher than the first temperature, wherein the substrate is functionalized according to the reaction scheme of FIG. 1.

2. The method of claim 1, wherein the acid functionalities participate in dehydration mechanisms of the glucose.

3. The method of claim 1, wherein the saccharide feedstock further comprises xylose for dehydration to furfural by the solid state catalytic structure.

4. The method of claim 1, wherein the first temperature is greater than 130° C.

5. The method of claim 1, wherein the saccharide feedstock is dissolved in an ionic liquid composition comprising a mixture of ionic liquid and water or aprotic solvent.

6. The method of claim 5, wherein the aprotic solvent is selected from the group consisting of valerolactone, acetonitrile and dimethylacetamide, and wherein the ionic liquid is present in the mixture in an amount of 20 vol. % to 80 vol. %.

7. A method of producing HMF and levulinic acid comprising:
   providing a solution comprising saccharide feedstock including cellulose in an ionic liquid composition at a first temperature;

bringing the saccharide feedstock solution into contact with a solid state catalytic structure comprising a substrate having one or more surfaces functionalized with saccharide solubilization functionalities and acid functionalities, wherein the saccharide solubilization functionalities comprise one or more imidazolium halide salts pendant along chains of a first polymeric species attached to the substrate surface, and wherein the acid functionalities comprise aryl sulfonic acid groups pendant along chains of a second polymeric species attached to the substrate surface;

hydrolyzing the cellulose with the acid functionalities of the solid state catalytic structure to provide glucose feedstock in the ionic liquid composition;

altering the temperature of the ionic liquid composition to a second temperature;

bringing the glucose feedstock into contact with the solid state catalytic structure to effectuate dehydration of the glucose to provide the HMF; and altering the temperature of the ionic liquid composition to a third temperature and bringing the HMF into contact with the solid state catalytic structure to produce levulinic acid, wherein the third temperature is higher than the second temperature, wherein the substrate is functionalized according to the reaction scheme of FIG. 1.

8. The method of claim 7, wherein the acid functionalities of the solid state catalytic structure participate in dehydration mechanisms of the glucose.

9. The method of claim 7, wherein the saccharide feedstock further comprises hemicellulose for hydrolysis by the acid functionalities into xylose feedstock.

10. The method of claim 9, wherein the xylose feedstock is brought into contact with the solid state catalytic structure at the second temperature to effectuate dehydration of the xylose to furfural.

11. The method of claim 7, wherein the ionic liquid composition comprises a mixture of ionic liquid and water or aprotic solvent.

12. The method of claim 11, wherein the aprotic solvent is selected from the group consisting of valerolactone, acetonitrile and dimethylacetamide.

13. The method of claim 11, wherein the ionic liquid is present in the mixture in an amount of 20 vol. % to 80 vol. %.

14. The method of claim 1, further comprising adding heterogeneous catalyst to the saccharide feedstock or the solid state catalytic structure, the heterogeneous catalyst comprising β-Sn or Sn/W.

15. The method of claim 1, wherein yield of the HMF is greater than 60%.

16. The method of claim 7, further comprising adding heterogeneous catalyst to the saccharide feedstock or the solid state catalytic structure, the heterogeneous catalyst comprising β-Sn or Sn/W.

17. The method of claim 1, wherein the dehydration of the glucose yields the HMF in an amount in excess of 60%.

18. The method of claim 1, wherein the levulinic acid is produced at a yield of 30-60 percent.

19. The method of claim 7, wherein the dehydration of the glucose yields the HMF in an amount in excess of 60%.

20. The method of claim 7, wherein the levulinic acid is produced at a yield of 30-60 percent.

* * * * *